US00PP22779P3

(12) United States Plant Patent
Zaiger et al.

(10) Patent No.: US PP22,779 P3
(45) Date of Patent: Jun. 12, 2012

(54) CHERRY TREE NAMED 'ROYAL TIOGA'

(50) Latin Name: *Prunus avium*
Varietal Denomination: Royal Tioga

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 182 days.

(21) Appl. No.: 12/802,026

(22) Filed: May 28, 2010

(65) Prior Publication Data

US 2011/0296569 P1 Dec. 1, 2011

(51) Int. Cl.
*A01H 5/00* (2006.01)

(52) U.S. Cl. ..... Plt./181

(58) Field of Classification Search ..... Plt./181
See application file for complete search history.

*Primary Examiner* — Kent L Bell

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Early blooming with a low winter chilling requirement of approximately 500 hours at or below 45° F.
2. Fruit maturing in the early season.
3. Fruit with an attractive red skin color.
4. Fruit with good flavor and eating quality.
5. Heavy and regular production of large size fruit.

1 Drawing Sheet

Botanical classification: *Prunus avium.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Royal Lee' Cherry (U.S. Plant Pat. No. 12,417), 'Minnie Royal' (U.S. Plant Pat. No. 12,942), 'Bing' Cherry (non-patented), 'Brooks' Cherry (U.S. Plant Pat. No. 6,676) and our proprietary seedling selections '25Z134' and '6GM73'.

STATEMENT REGARDING FEDERALLY SPONSORED RESEARCH AND DEVELOPMENT

Not applicable.

ORIGIN OF THE VARIETY

The present new variety of cherry tree (*Prunus avium*) was originated by us in our experimental orchard located near Modesto, Calif. as a first generation cross between our selected proprietary seedlings '25Z134' and '6GM73'. The seed parent (25Z134) originated as a first generation cross between an open pollinated seedling of 'Bing' Cherry (non-patented) and 'Royal Lee' Cherry (U.S. Plant Pat. No. 12,417). The pollen parent (6GM73) originated as a second generation cross between a selected proprietary seedling from an open pollinated 'Bing' Cherry and 'Minnie Royal' Cherry tree (U.S. Plant Pat. No. 12,942). A large group of these first generation crosses were budded on older trees of 'Mahaleb' Rootstock (non-patented) to accelerate earlier fruit production for evaluation. Under close and careful observation, one such seedling, which is the present variety, exhibited desirable fruit characteristics and was selected for additional asexual propagation and commercialization.

ASEXUAL REPRODUCTION OF THE VARIETY

Asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct cherry tree is of large size, vigorous, upright growth, and has a low winter chilling requirement of approximately 500 hours at or below 45° F. The tree is a regular and productive bearer of large size fruit that ripens in the early maturity season. The fruit is further characterized by having an attractive red skin color, good flavor and eating quality, with firm flesh, good storage and handling quality. In comparison to its seed parent (25Z134) the tree blooms approximately 10 days earlier and the fruit ripens approximately 20 days earlier. In comparison to its pollen parent (6GM73) the fruit of the new variety ripens approximately 7 days earlier and is larger in size. In comparison to the commercial cherry variety 'Brooks' (U.S. Plant Pat. No. 6,676) the fruit of the new variety ripens approximately 24 days earlier.

PHOTOGRAPH OF THE VARIETY

The accompanying color photographic illustration shows typical specimens of the foliage and fruit of the present new cherry variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 6 year old specimens grown near Modesto, Calif., with color in accordance with Munsell Book of Color.

Tree:

*Size.*—Large. Pruned to 3.0 to 3.5 meters in height and width for economical harvesting of fruit, varies with different cultural practices.

*Vigor.*—Vigorous, tree growth of 1.5 to 2.0 meters in height the first growing season. Growth rate will vary with types of soil, fertility and cultural practices.

*Form.*—Upright, usually pruned to vase shape.

*Branching habit.*—Upright. Crotch angle approximately 35°, increases with heavy crop load.

*Productivity.*—Productive, produces heavy crop annually. Similar in production to the commercial cherry variety 'Bing' (non-patented) of approximately 60 to 100 pounds per tree depending on the size of the tree and the climatic conditions.

*Bearer.*—Regular, heavy fruit set 4 consecutive years. Set varies with climatic conditions at bloom time. No alternate bearing observed.

*Fertility.*—Self-fertile, heavy fruit set under bag when pollinated with own pollen.

*Density.*—Medium dense, controlled by pruning.

*Hardiness.*—Hardy in all stone fruit growing areas of California. Tree grown in USDA Hardiness Zone 9. Winter chilling requirement is approximately 500 hours at or below 45° F.

Trunk:

*Size.*—Large. Average circumference of 50.8 cm at 20.3 cm above ground on a 6 year old tree.

*Stocky.*—Medium stocky.

*Texture.*—Medium rough, roughness increases with age of tree.

*Color.*—Varies from 10YR 3/2 to 2.5Y 4/2.

Branches:

*Scaffold branch.*—Size — medium stocky. Average circumference 15.0 cm at 1.3 meters above ground. Crotch angle approximately 35°, increases with heavy crop load. Surface Texture — old growth medium rough, roughness increases with age of growth. Lenticels — average 18 in a 25.8 sq cm area of branch. Average length 7.8 mm. Average width 2.1 mm. Color varies from 2.5Y 6/10 to 5Y 7/8. Color — old growth varies from 10YR 5/6 to 7.5YR 2/4, varies with age of growth.

*Fruiting branches.*—Average length 27.4 cm. Average diameter 4.2 mm. Texture relatively smooth to medium rough. Color varies from 10YR 6/2 to 10YR 5/2.

*Current season branches.*—Average length 47.8 cm. Average diameter 4.8 cm. New growth relatively smooth. Color varies from 2.5GY 5/8 with 7.5R 3/4 where exposed to the sun.

Leaves:

*Size.*—Large. Average length 155.9 mm. Average width 68.2 mm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins, glabrous. Lower surface relatively smooth, small ridges created by midrib and pinnate venation, glabrous.

*Petiole.*—Average length 37.6 mm. Average width 2.3 mm. Color varies from 2.5GY 5/4 to 7.5R 2/4. Shallow, longitudinal groove. Glabrous.

*Glands.*—Reniform. Size — large. Average length 2.8 mm. Average width 1.9 mm. Average number 2, varies from 1 to 3. Located primarily on the upper portion of the petiole and on the base of the leaf blade. Color varies from 7.5R 3/8 to 7.5R 3/10.

*Stipules.*—Average number — 2. Average length 12.2 mm. Edges serrulate. Color 5GY 5/6 with 7.5R 3/6 on edges.

*Color.*—Upper surface varies from 2.5GY 3/4 to 7.5GY 4/6. Lower surface varies from 2.5GY 5/4 to 10GY 5/4. Midvein color 10Y 7/4 with 7.5R 4/6.

Flower buds:

*Size.*—Medium to large. Average length 17.1 mm. Average diameter 9.7 mm.

*Hardiness.*—Hardy with respect to California winters.

*Form.*—Plump, conical, becoming elongated just before opening.

*Pedicel.*—Average length 14.7 mm. Average width 1.2 mm. Color varies from 2.5GY 5/6 to 2.5GY 5/8.

*Color.*—N 9.5/ (white), edged with 2.5R 6/6 to 5R 6/4 along upper surface of petals, color fades to white as buds open.

*Number of buds per spur.*—Average 10, varies from 5 to 13.

Flowers:

*Blooming period.*—Date of First Bloom Feb. 25, 2010. Date of Petal Fall Mar. 6, 2010, varies slightly with climatic conditions.

*Size.*—Medium to large. Average height 19.6 mm. Average diameter 30.1 mm.

*Petals.*—Normally 5, alternately arranged to the sepals. Nearly orbicular, narrows at point of attachment. Margin — sinuate. Average length 16.1 mm. Average width 15.5 mm. Both upper and lower surfaces glabrous. Color — N 9.5/ (white).

*Sepals.*—Normally 5, alternately arranged to the petals. Triangular shape. Margin — entire. Both upper and lower surfaces glabrous. Average length 6.7 mm.

Average width 4.8 mm. Color — upper surface varies from 2.5GY 6/6 to 5GY 5/6. Lower surface varies from 5GY 5/6 to 5R 3/4.

*Stamens.*—Average number per flower 34. Average filament length 13.2 mm. Filament color N 9.5/ (white). Anther color varies from 5Y 8/8 to 7.5Y 7/8.

*Pollen.*—Self-fertile, heavy fruit set under bag when pollinated with own pollen. Color varies from 2.5Y 7/10 to 5Y 7/10.

*Pistil.*—Normally one. Average length 15.0 mm. Position of stigma an average of 1.7 mm below anthers. Surface — glabrous. Color varies from 2.5GY 6/6 to 5GY 5/8.

*Fragrance.*—Moderate.

*Color.*—N 9.5/ (white).

*Number flowers per flower bud.*—Average 3, varies from 1 to 4.

*Pedicel.*—Average length 22.5 mm. Average width 1.2 mm. Color varies from 2.5GY 6/6 to 5GY 5/8.

Fruit:

*Maturity when described.*—Firm ripe.

*Date of first picking.*—Apr. 28, 2010.

*Date of last picking.*—May 6, 2010, varies slightly with climatic conditions.

*Size.*—Large. Average diameter axially 25.9 mm. Average transversely in suture plane 24.0 mm. Average weight 8.5 grams, varies slightly with fertility of the soil, amount of thinning and climatic conditions.

*Form.*—Globose.

*Sutures.*—Nearly smooth, extends from base to apex.

*Ventral surface.*—Nearly smooth.

*Apex.*—Rounded to slightly retuse.

*Base.*—Retuse.

*Stem cavity.*—Rounded. Average depth 1.3 mm. Average diameter 3.8 mm.

Stem:

*Size.*—Large. Average length 40.3 mm. Average diameter 1.8 mm.

*Color.*—Varies from 2.5GY 5/8 to 5GY 5/4.

Flesh:

*Ripens.*—Slightly earlier at apex.

*Texture.*—Very firm.

*Fibers.*—Few, small, tender.

*Firmness.*—Very firm.

*Aroma.*—Slight.

*Amydgalin.*—Undetected.

*Eating quality.*—Very good.

*Flavor.*—Very good, good balance between acid and sugar.

*Juice.*—Moderate amount, enhances flavor.

*Brix.*—Average 16.5°, varies slightly with amount of fruit per tree and climatic conditions.

*Color.*—Varies between 2.5Y 8.5/2 and 5R 3/8.

Skin:

*Thickness.*—Medium.

*Surface.*—Smooth.

*Bloom.*—Wanting.

*Tendency to crack.*—None during dry weather. Very slight tendency to crack during wet weather, varies with stage of maturity.

*Color.*—Varies from 7.5R 3/10 to 7.5R 2/8.

*Tenacity.*—Tenacious to flesh.

*Astringency.*—Undetected.

Stone:

*Type.*—Clingstone.

*Size.*—Medium. Average length 12.2 mm. Average width 9.5 mm. Average thickness 7.4 mm.

*Form.*—Obovoid.

*Base.*—Flat to slightly rounded.

*Apex.*—Very slight apical point. Average length 0.6 mm.

*Surface.*—Very slightly pitted throughout. Small ridges run along each side of the suture line from base to the apex.

*Sides.*—Varies from equal to unequal with one side extending further from the suture plane.

*Tendency to split.*—None.

*Color.*—Varies from 10YR 6/6 to 2.5Y 6/6 when dry.

*Pit cavity.*—Average length 12.4 mm. Average depth 3.8 mm.

Kernel:

*Size.*—Small. Average length 8.2 mm. Average width 6.0 mm. Average depth 4.9 mm.

*Form.*—Ovate.

*Viability.*—Partially viable, incomplete embryos in some stones.

*Skin color.*—Varies from 2.5Y 8.5/4 to 5Y 9/4.

Use: Dessert.

*Market.*—Local and long distance.

Keeping quality: Good, held firm in cold storage 2 weeks at 38° to 42° F. without internal breakdown of flesh, shriveling or appreciable loss of flavor.

Shipping quality: Good, showed minimal flesh bruising or skin scarring during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of cherry tree, substantially as illustrated and described.

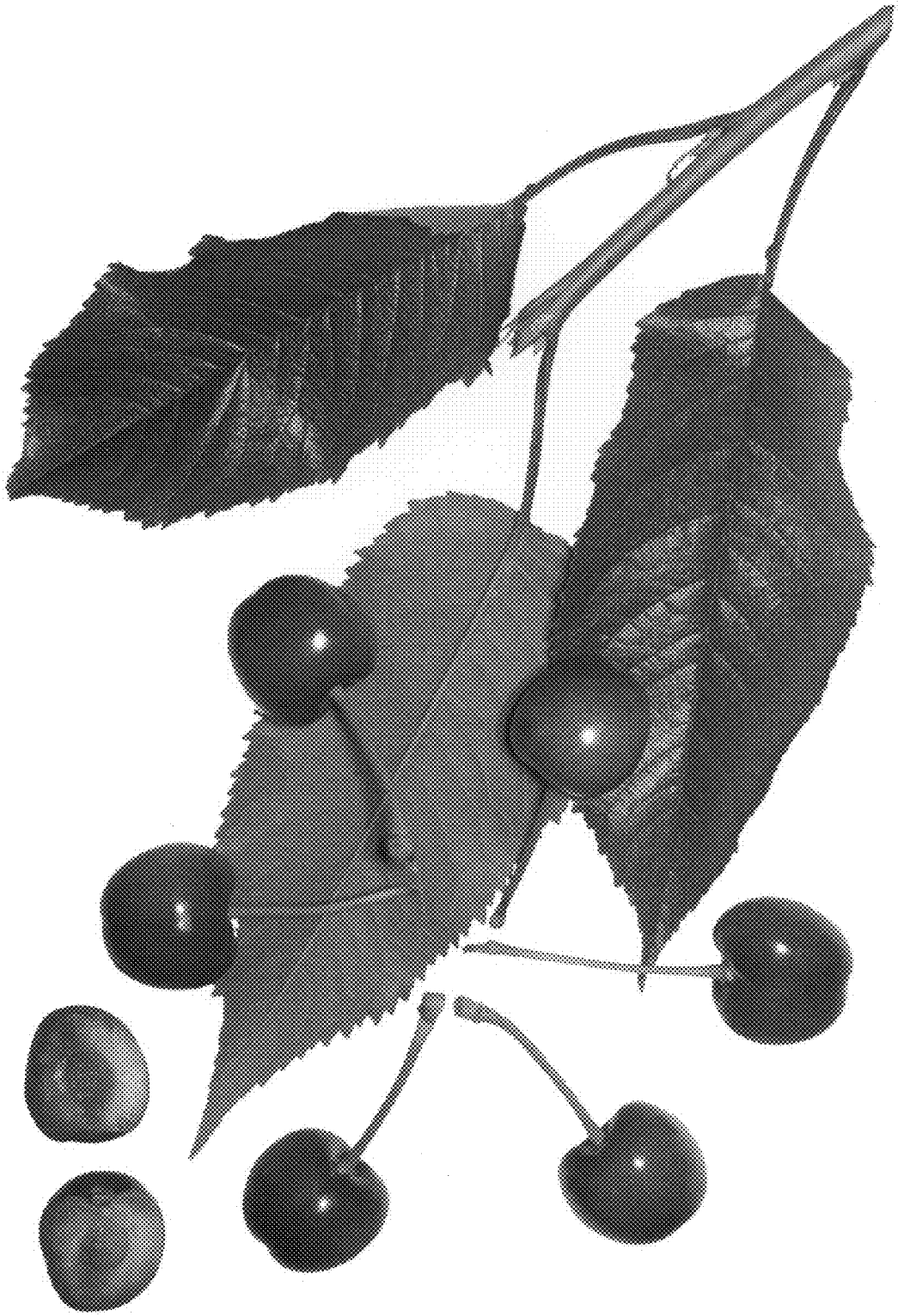

* * * * *